United States Patent
Ticsa

(10) Patent No.: US 7,379,605 B1
(45) Date of Patent: May 27, 2008

(54) METHOD FOR THE INTEGRATION OF MEDICAL IMAGING DATA AND CONTENT FOR WIRELESS TRANSMISSION AND REMOTE VIEWING

(76) Inventor: Stelian Doru Ticsa, 2820 Newbern Way, Clearwater, FL (US) 33761

( * ) Notice: Subject to any disclaimer, the term of this patent is extended or adjusted under 35 U.S.C. 154(b) by 880 days.

(21) Appl. No.: 10/711,303

(22) Filed: Sep. 9, 2004

Related U.S. Application Data

(60) Provisional application No. 60/481,345, filed on Sep. 9, 2003.

(51) Int. Cl.
*G06K 9/36* (2006.01)
*G06K 9/46* (2006.01)

(52) U.S. Cl. .................................................... 382/232

(58) Field of Classification Search ................ 382/100, 382/128, 232, 233, 240; 709/203, 247
See application file for complete search history.

(56) References Cited

U.S. PATENT DOCUMENTS

| | | | |
|---|---|---|---|
| 6,314,452 B1 * | 11/2001 | Dekel et al. ................. | 709/203 |
| 6,711,297 B1 | 3/2004 | Chang et al. | |
| 6,925,208 B1 * | 8/2005 | Huffman ..................... | 382/232 |

OTHER PUBLICATIONS

Retain TEN-IBC B3012 Deliverable D7: Second Guidelines for TEN-IBC in Medical Imaging, OFFIS, Feb. 1997, pp. 1-25.

* cited by examiner

*Primary Examiner*—Phuoc Tran
(74) *Attorney, Agent, or Firm*—Anton J. Hopen; Smith & Hopen, P.A.

(57) ABSTRACT

A method of transmitting medical imaging data files over high latency low bandwidth networks by using an incremental RSYNC protocol over an encrypted connection.

7 Claims, 4 Drawing Sheets

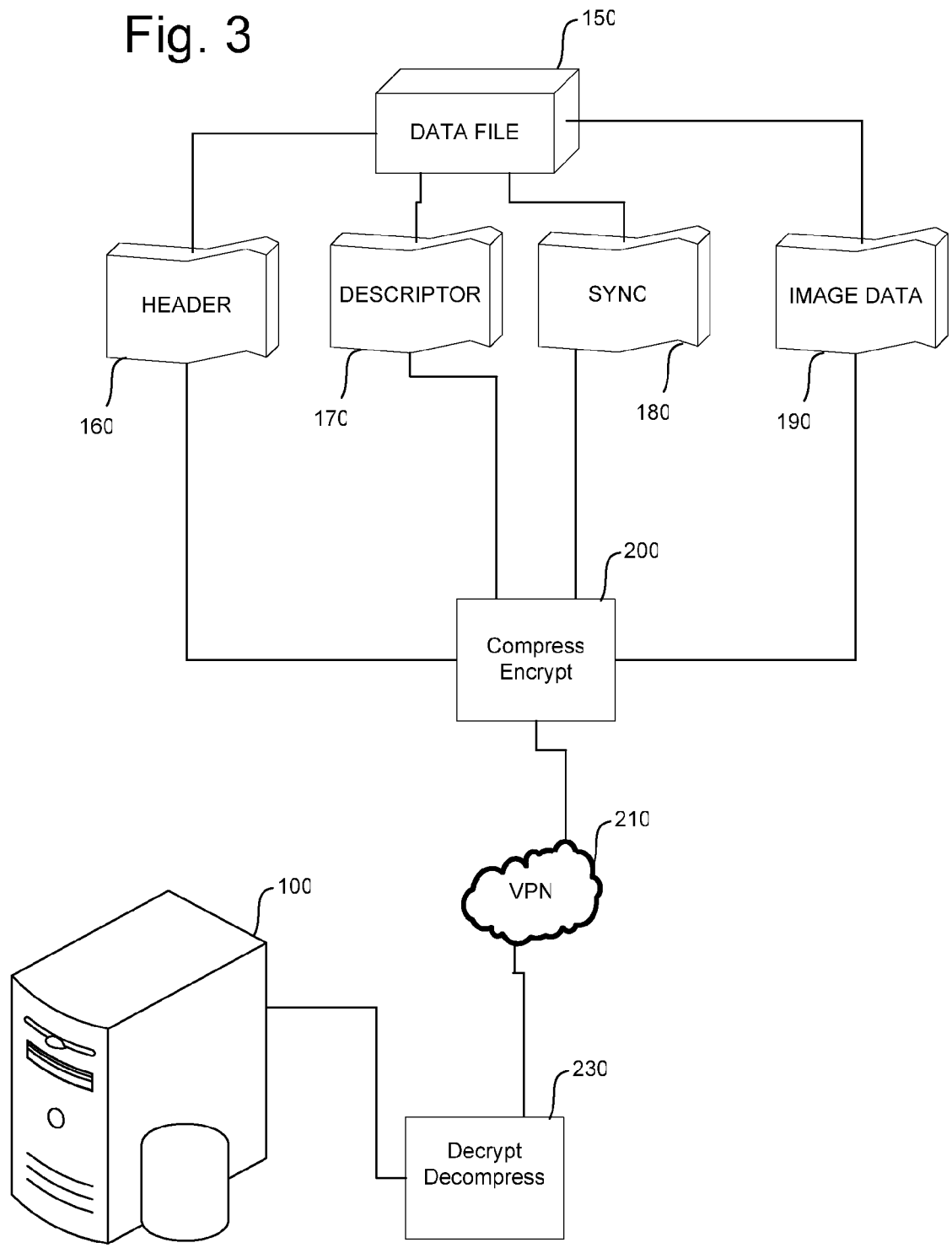

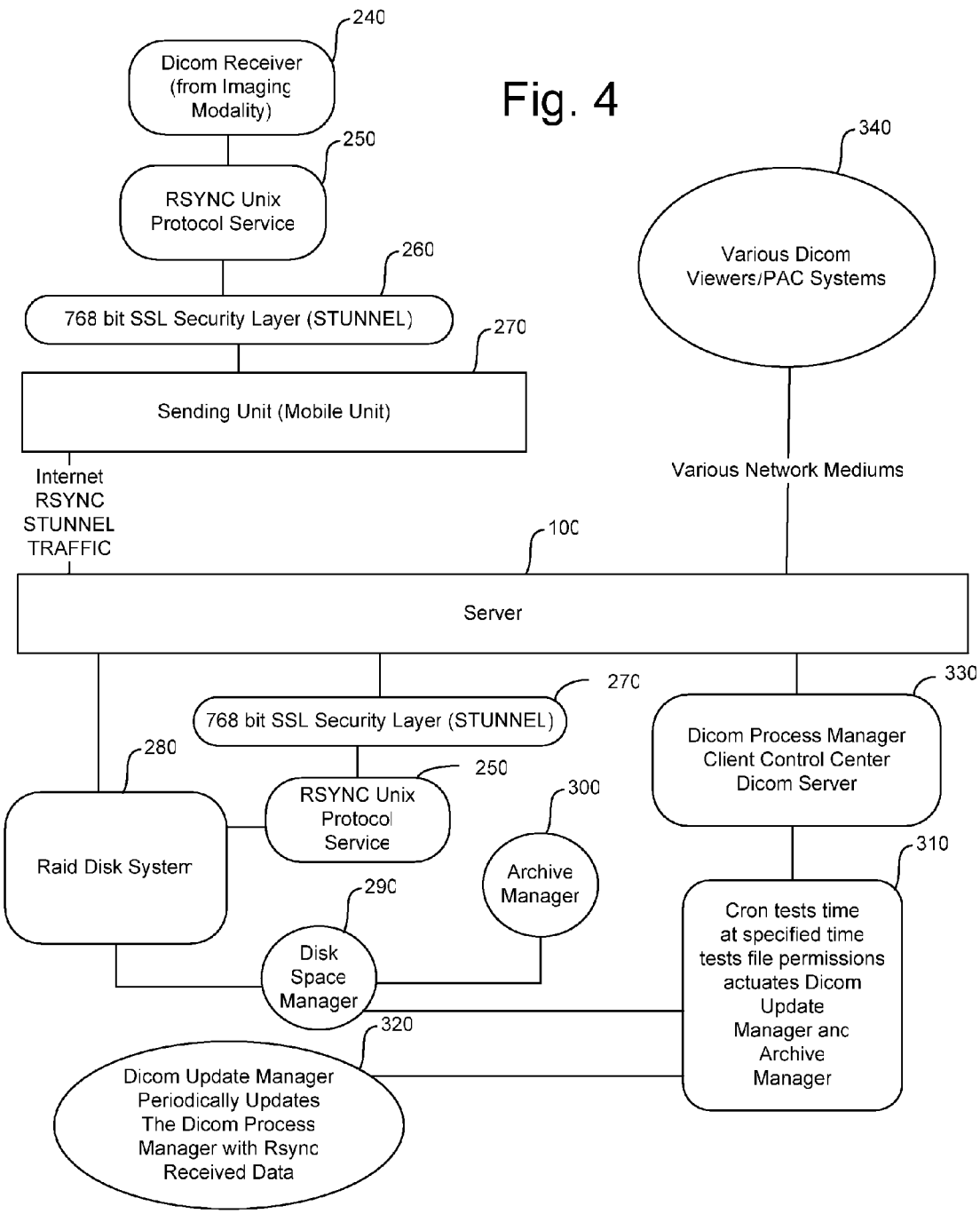

METHOD FOR THE INTEGRATION OF MEDICAL IMAGING DATA AND CONTENT FOR WIRELESS TRANSMISSION AND REMOTE VIEWING

PRIORITY CLAIM

This invention claims priority from U.S. Provisional Patent Ser. No. 60/481,345 filed Sep. 9, 2003 and titled "Method for the Integration of Medical Imaging Data and Content for Wireless Transmission and Remote Viewing."

FIELD OF INVENTION

This invention relates to a system for the acquisition and verification of the integrity of medical imaging data for encrypted transmission via wireless VPN network and embedding upon a CD-ROM.

BACKGROUND OF INVENTION

The advent of digital imaging for the purpose of medical diagnosis has resulted in a variety of scanning systems and image formats. The comparative ease of manipulating these digital images is obviated by problems arising from incompatible software among the various manufacturers of the imaging scanners.

In response to the increase in digital imaging technology, the American College of Radiology (ACR) and the National Electrical Manufacturers Association (NEMA) developed the Digital Imaging and Communications in Medicine (DI-COM) standard. The standard seeks to make uniform the transferring of medical images and information between viewing and scanning sources. The goal of DICOM is to allow users of imaging hardware from different manufacturers to share information.

Despite the creation of the DICOM standard manufacturers have developed proprietary software, and image formats, which complicate the transmission and viewing of digital images that are created on one machine but need to be viewed on another. Modern machines contain a Picture Archiving and Communications System (PACS) which is responsible for the storage and downloading of digital images. Data sent from an incompatible machine which is not in a recognizable format by the receiving machine is not downloaded. The incompatibility is created, not when the image is scanned, but when the information is converted from the scanning source's hard drive by the manufacturer's propriety software.

As a result, Doctors are often unable to view digital images captured by scanning technicians. If the technician reduces the image to a tangible picture the Doctor cannot manipulate the image to zoom in, rotate, or change the contrast of the still image. Furthermore, the process of reducing the images to tangible form is costly in both time and materials.

SUMMARY OF THE INVENTION

The present invention is a method of transmitting medical diagnostic imaging over low-speed wireless networks to remote locations including the steps of: accessing an imaging modality; receiving an image from the imaging modality; establishing a wireless connection with a remote primary server; establishing a security layer over the remote connection; compressing the image; encrypting the compressed image; establishing an incremental file transfer of the compressed image over the security layer to the primary server; transmitting the compressed image to the primary server; decrypting the compressed image; decompressing the image; substantially losslessly storing the image on a storage device local to the primary server; accepting authenticated remote inbound requests for viewing the image; and sending the image to an authenticated requestor. The at least one image received from the imaging modality is preferably formatted to a DICOM specification and the connection with the remote primary server is through TCP/IP. The protocol for the incremental file transfer is an RSYNC-based protocol and may include the step of archiving the at least one image to an optical storage medium for long term storage.

Another embodiment of the invention is a method of transmitting medical diagnostic imaging wirelessly to remote locations comprising the steps of: providing a client computer; providing a DICOM receiver module communicatively coupled to the client computer, the DICOM receiver adapted to accept DICOM images and patient information from imaging modalities for manipulation and filming; providing a RSYNC module communicatively coupled to the client computer; providing a GZIR compression module adapted to compress data transmitted by the RSYNC module; providing a secure socket layer module communicatively coupled to the RSYNC module, the secure socket layer module adapted to encrypt data transmitted by the RSYNC module; providing a wireless network interface communicatively coupled to the client computer; providing a primary server; receiving the encrypted transmission on the primary server, decrypting the transmission, and storing the DICOM images.

Yet another embodiment of the invention is a method of transmitting medical diagnostic imaging to remote locations comprising the steps of: receiving a DICOM data file on a client; parsing the DICOM data file for a data header, image descriptor, sync value and image data; establishing a secure connection between the client and a remote server; verifying an absence of a duplicate DICOM data file on the remote server; transmitting the DICOM data file from the client to the remote server responsive to the absence of a duplicate DICOM data file on the remote server.

BRIEF DESCRIPTION OF THE DRAWINGS

FIG. 3 is a diagrammatic view of header parsing and transmission according to an embodiment of the invention.

FIG. 4 is a diagrammatic view of a specific implementation of the invention according to an embodiment of the invention.

DETAILED DESCRIPTION OF PREFERRED EMBODIMENT

Figure 1:
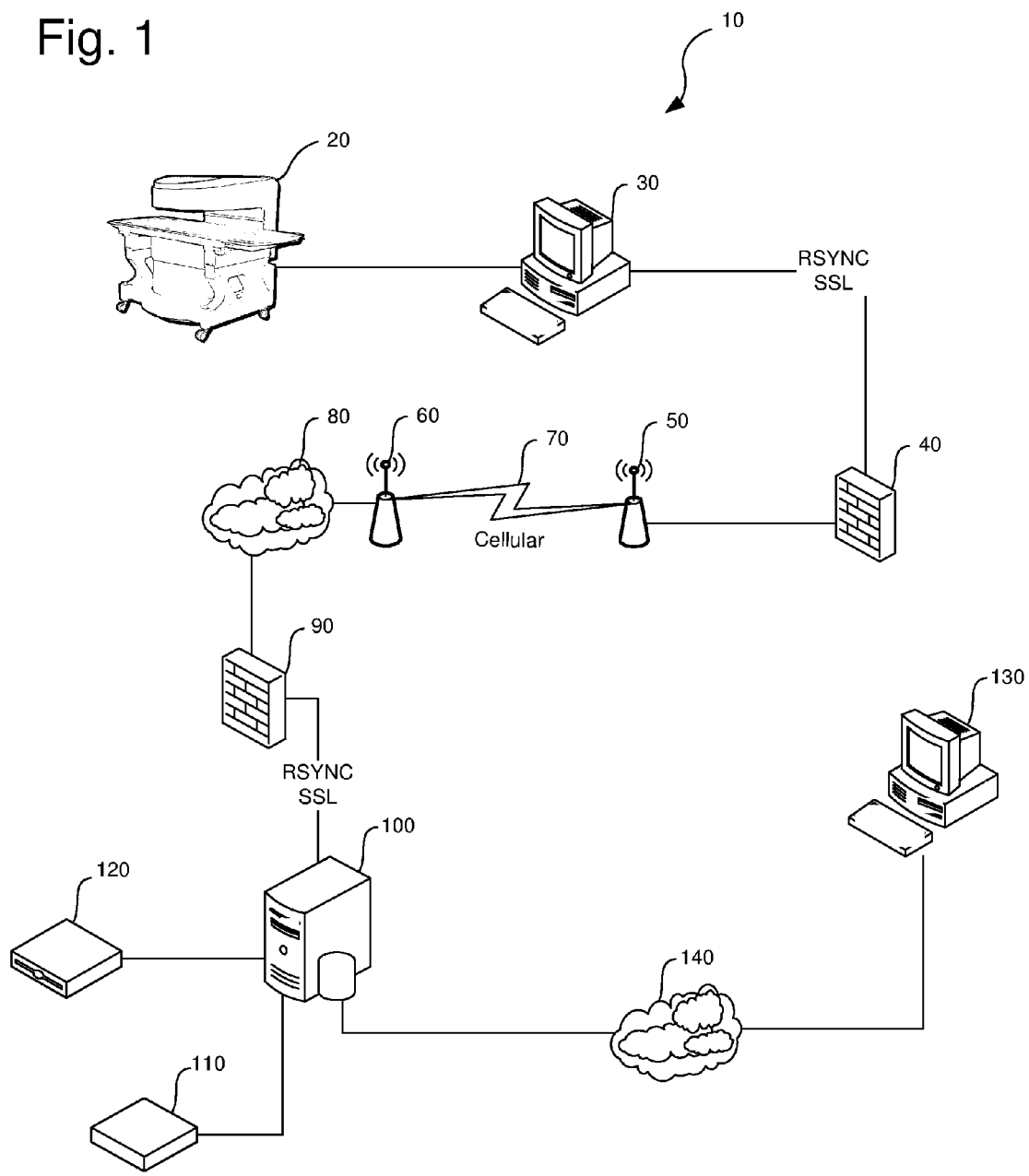
FIG. 1 is a diagrammatic view of an embodiment of the invention.

Turning to FIG. 1, the invention is denoted numeral 10 as a whole. Imaging modality 20 generates a DICOM data file received by client computer 30. Client computer 30 establish first security layer 40 including SSL-based encryption over an RSYNC incremental protocol. The RSYNC protocol allows the resumption of the stream data over high latency, low bandwidth networks that occasionally fail. Absent this incremental protocol, a network failure, even if brief, or if a single packet in a transfer times out, the sender or server point must restart the transmission from the beginning.

Because the DICOM data files may be necessarily large, even when compressed, the RSYNC protocol is advantageous as it permits the transmission of the files through relatively unstable network connections.

First wireless transceiver 50 transmits to second wireless transceiver 60 through wireless network 70. Wireless network 70 may include, but is not limited to, cellular networks, WiFi, Bluetooth, or any other established protocol capable of transmitting data. As noted above, an advantage of the present invention is the incremental protocol which permits use of cellular networks, traditionally unfavored for the secure transmission of large files.

First WAN 80 communicates the DICOM data file from the second wireless transceiver 60 to second security layer 90. Primary server 100 is communicatively coupled to second security layer 90 and may store the DICOM data file on local storage device 110 or archive the data file onto an optical driver 120. Authenticated requestor 130 accesses the DICOM data file from primary server 100 through a secure second WAN 140 connection, preferably a VPN or an equivalent thereof.

Figure 2:
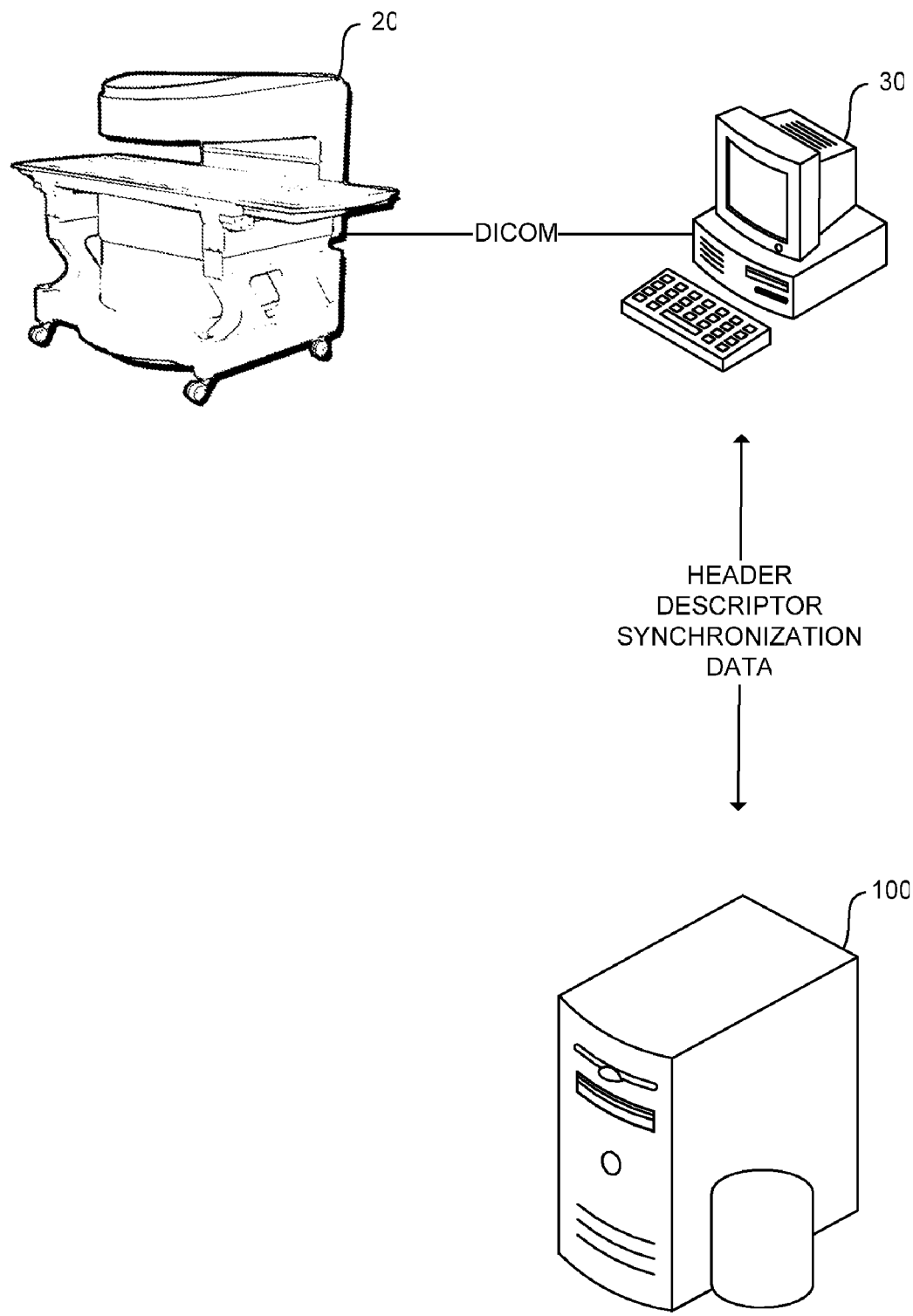
FIG. 2 is a diagrammatic view of a synchronization step between client and server according to an embodiment of the invention.

An important feature of the DICOM format is the header information. In FIG. 2, imaging modality 20 transfers DICOM data file to client computer 30. Client computer 30 parses from the DICOM data file, header, descriptor, synchronization data and image data. The parsed information is analyzed by primary server to verify data integrity and detect duplicate images. The process is shown in more detail in FIG. 3 wherein DICOM data file 150 is parsed into header 160, descriptor 170, synchronization data 180 and image data 190. The parsed elements are compressed an encrypted 200 then transmitted through VPN 210. They parsed elements are decrypted and decompressed 230 at primary server 100.

FIG. 4 shows an implementation of the present invention. Dicom receiver 240 is communicatively coupled to RSYNC Unix protocol service 250. SSL security layer 260 encrypts RSYNC Unix protocol service 250 at sending unit 270 for transmission to server 100 where it is stored on RAID 280. Disk space manager 290 and archive manager 300 monitor conditions of RAID 280 and administer the storage collection accordingly. Cron 310 tests time at specified interval, tests file permissions, actuates DICOM update manager 320 and archive manager 300. DICOM update manager 320 periodically updates the DICOM process manager 330 with RSYNC received data. DICOM process manager 330 includes client control center for establishing authenticated access from various DICOM viewers/PAC systems 340 to primary server 100.

The present invention provides an integrated system wherein the image data is retrieved directly from the scanning source's hard drive, formatted into a common specification, and then distributed to remote locations.

The invention also enables the transmission of the image data over a secure wireless virtual private network. This allows transmission from any location where the transmitting party has access to a cellular network and obviates the need for a landline connection. The data is compressed before transmission allowing for high transfer rates over the cellular network.

In an alternative embodiment of the invention, formatted data is distributed onto a computer readable optical disc, CD-ROM, which is dramatically less expensive than proprietary media created specially for medical digital images.

These and other embodiments of the invention are achieved by acquisition and verifying the integrity of data, while maintaining a record of the data sent at the server side. Communication of this data is done through a compressed virtual private network pipe with variable levels of encryption from 64 bit up to 512 even 1024 bit encryption by using a secured socket connection based on, but not necessarily completely compatible with SSL.

Included in this invention is the ability to embed the medical data to a CD-ROM in a manner that allows the data to be viewed in any modern IBM compatible PC that is properly configured, and the means to view those images in a way that is pleasing to each individuals viewing needs, making the images more "palatable" to the eyes of each of the authorized viewers, while at the same time giving the viewer the ability to determine the origin, meaning, and patient information, from the image header to more quickly make a diagnosis and expedite a course of action with the other concerned parties, in reference to the images intended audience.

First the data is analyzed, and is broken down into its chief components including the image header, the image descriptor (containing information regarding the image type), the image synchronization data, and the image data. Then this data is sent through a chain of events including determining the duplicity of the data at the server side of the connection, explaining to the server what is being sent, sending the data header, sending the image descriptor, then sending the image synchronization data, and sending the image data.

The send process for each event is dealt with in the following order. First the receiving modality's true global IP address is determined. Then a socket connection to the modality's global IP address is created. A SI0 VPN connection is made to the receiving modality and a Non-Global Local connection to the modality through this encrypted pipe is established.

The IP's to be used for this connection are negotiated, establishing the client-side IP and the server-side IP followed by a test VPN DSN data connection. There is then a request security level for the connection; the user name and password are sent. The server then verifies user name and password. Upon verification the pipe is secured and the DICOM modality begins synchronization. If the user name and password do not match, then the connection is closed and the connection is refused from the calling IP for a specified amount of time.

The Telerad requests that the called modality AE respond to its call with an echo and the DICOM server responds with an ECHO if it is present and alive otherwise the connection is closed. The Telerad begins the process described above to send each image individually through this connection, while compressing the data, at or near 110 kbps per second or 13 KBps. After sending all this data the Telerad sends another echo request and closes the socket connection to the server to allow other connections to occur.

The linking process is comprised of the execution of the following software application stream:
 1) TIANT JDICOM Java Based DICOM Toolkit software
 2) Sun Microsystems JAVA Runtime environment Version 1.4
 3) Windows XP Professional (server side)
 4) DEBIAN LIVE LINUX Kernel Version 2.4.3
 5) KDE 3 Desktop environment software
 6) Fingerprint protection software and biometric authentication solution by Digital Persona
 7) \VINE 2.099.b6e.i386.rc4343.build63067 Windows NT emulation technology for Linux
 8) DICOMWorks 1.3.7 or later Viewer software
 9) Nero Burning ROM version 6.0 or later 10) Proprietary linking software for older modalities
11) Image enhancement software
12) Video capture software for the retrieval of images and other video based DICOM sources (needs may vary the software used)
13) DICOM video file conversion software namely Tomo-Vision, DICOMatic and others
14) A unique Linux caching mechanism allowing the full copy protection (source available)
15) Reiser 3 file system for redundant file storage, data protection, files copy protection and accountability
16) Xitami web server software
17) Xitami FTP transfer software
18) Telnet and SSH servers

| | |
|---|---|
| 10 | Invention as a whole |
| 20 | Imaging modality |
| 30 | Client computer |
| 40 | First security layer |
| 50 | First wireless transceiver |
| 60 | Second wireless transceiver |
| 70 | Wireless network |
| 80 | First WAN |
| 90 | Second security layer |
| 100 | Primary server |
| 110 | Local storage device |
| 120 | Optical drive |
| 130 | Authenticated requestor |
| 140 | Second WAN |
| 150 | DICOM data file |
| 160 | Header |
| 170 | Descriptor |
| 180 | Synchronization data |
| 190 | Image data |
| 200 | Compression & encryption |
| 210 | VPN |
| 230 | Decryption & decompression |
| 240 | DICOM receiver |
| 250 | RSYNC Unix protocol service |
| 260 | SSL security layer |
| 270 | Sending unit |
| 280 | RAID |
| 290 | Disk space manager |
| 300 | Archive manager |
| 310 | Cron |
| 320 | Dicom update manager |
| 330 | Dicom process manager |
| 340 | Various Dicom viewers/PAC systems |

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of transmitting medical diagnostic imaging over low-speed wireless networks to remote locations comprising the steps of: accessing an imaging modality; receiving an image from the imaging modality; establishing a wireless connection with a remote primary server; establishing a security layer over the remote connection; compressing the image; encrypting the compressed image; establishing an incremental file transfer of the compressed image over the security layer to the primary server; transmitting the compressed image to the primary server; decrypting the compressed image; decompressing the image; substantially losslessly storing the image on a storage device local to the primary server; accepting authenticated remote inbound requests for viewing the image; and sending the image to an authenticated requestor.

2. The method of claim 1 wherein the at least one image received from the imaging modality is formatted to a DICOM specification.

3. The method of claim 1 wherein the connection with the remote primary server is through TCP/IP.

4. The method of claim 1 wherein protocol for the incremental file transfer is an RSYNC-based protocol.

5. The method of claim 1 further comprising the step of archiving the at least one image to an optical storage medium for long term storage.

6. A method of transmitting medical diagnostic imaging wirelessly to remote locations comprising the steps of: providing a client computer; providing a DICOM receiver module communicatively coupled to the client computer, the DICOM receiver adapted to accept DICOM images and patient information from imaging modalities for manipulation and filming; providing a RSYNC module communicatively coupled to the client computer; providing a GZIR compression module adapted to compress data transmitted by the RSYNC module; providing a secure socket layer module communicatively coupled to the RSYNC module, the secure socket layer module adapted to encrypt data transmitted by the RSYNC module; providing a wireless network interface communicatively coupled to the client computer; providing a primary server; receiving the encrypted transmission on the primary server, decrypting the transmission, and storing the DICOM images.

7. A method of transmitting medical diagnostic imaging to remote locations comprising the steps of: receiving a DICOM data file on a client; parsing the DICOM data file for a data header, image descriptor, sync value and image data; establishing a secure connection between the client and a remote server; verifying an absence of a duplicate DICOM data file on the remote server; transmitting the DICOM data file from the client to the remote server responsive to the absence of a duplicate DICOM data file on the remote server.

* * * * *